United States Patent
Shutoh et al.

(10) Patent No.: US 10,329,403 B2
(45) Date of Patent: Jun. 25, 2019

(54) RESIN COMPOSITION, RESIN SHEET, RESIN CURED PRODUCT, AND RESIN SUBSTRATE

(71) Applicant: TDK CORPORATION, Tokyo (JP)

(72) Inventors: Hiroshi Shutoh, Tokyo (JP); Masaaki Yamashita, Tokyo (JP); Tsuyoshi Sugiyama, Tokyo (JP)

(73) Assignee: TDK CORPORATION, Tokyo (JP)

( * ) Notice: Subject to any disclaimer, the term of this patent is extended or adjusted under 35 U.S.C. 154(b) by 0 days.

(21) Appl. No.: 15/561,741

(22) PCT Filed: Apr. 28, 2016

(86) PCT No.: PCT/JP2016/063399
§ 371 (c)(1),
(2) Date: Sep. 26, 2017

(87) PCT Pub. No.: WO2016/175296
PCT Pub. Date: Nov. 3, 2016

(65) Prior Publication Data
US 2018/0105674 A1  Apr. 19, 2018

(30) Foreign Application Priority Data

Apr. 25, 2016 (JP) ................................. 2016-086708

(51) Int. Cl.
| | |
|---|---|
| *C08G 59/62* | (2006.01) |
| *C08L 63/00* | (2006.01) |
| *B32B 27/26* | (2006.01) |
| *B32B 27/38* | (2006.01) |
| *C08K 5/13* | (2006.01) |
| *C07C 39/15* | (2006.01) |

(52) U.S. Cl.
CPC ................ *C08K 5/13* (2013.01); *C08G 59/62* (2013.01); *C08L 63/00* (2013.01); *B32B 27/38* (2013.01); *C07C 39/15* (2013.01)

(58) Field of Classification Search
None
See application file for complete search history.

(56) References Cited

U.S. PATENT DOCUMENTS

| | | | |
|---|---|---|---|
| 3,644,538 A | 2/1972 | Starnes | |
| 5,300,559 A | 4/1994 | Sheehan et al. | |
| 5,300,698 A | 4/1994 | Aslam et al. | |
| 6,746,666 B1 * | 6/2004 | Luther ................. | A61K 8/492 424/400 |
| 2015/0118498 A1 * | 4/2015 | Sugiyama .............. | C08G 59/56 428/413 |
| 2015/0329695 A1 * | 11/2015 | Shimizu ................. | C08K 5/18 523/456 |

FOREIGN PATENT DOCUMENTS

| | | |
|---|---|---|
| EP | 2 871 196 A1 | 5/2015 |
| EP | 2 944 670 A1 | 11/2015 |
| JP | H11-323162 A | 11/1999 |
| JP | 2013-010919 A | 1/2013 |
| WO | 93/14140 A1 | 7/1993 |
| WO | 93/15063 A1 | 8/1993 |

OTHER PUBLICATIONS

Aug. 16, 2018 European Search Report issued in European Patent Application No. 16786572.4.

* cited by examiner

*Primary Examiner* — Michael J Feely
(74) *Attorney, Agent, or Firm* — Oliff PLC

(57) ABSTRACT

A resin composition includes an epoxy compound, a first triphenylbenzene compound, and a second triphenylbenzene compound. A ratio M (mol %) expressed by M (mol %)= (M1/M2)×100 is from 0.2 mol % to 16.3 mol %, where M1 is the number of moles (mol) of an alkoxy group contained in the second triphenylbenzene compound, and M2 is sum of the number of moles (mol) of a hydroxyl group contained in the first triphenylbenzene compound, the number of moles (mol) of the hydroxyl group contained in the second triphenylbenzene compound, and the number of moles (mol) of the alkoxy group contained in the second triphenylbenzene compound.

12 Claims, 2 Drawing Sheets

[ FIG. 1 ]
[ FIG. 2 ]
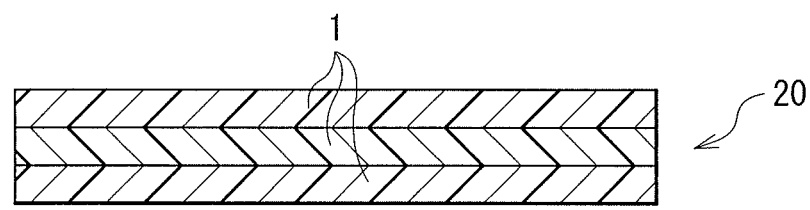
[ FIG. 3 ]
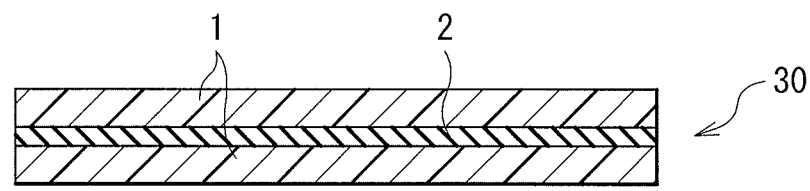
[ FIG. 4 ]
[ FIG. 5 ]
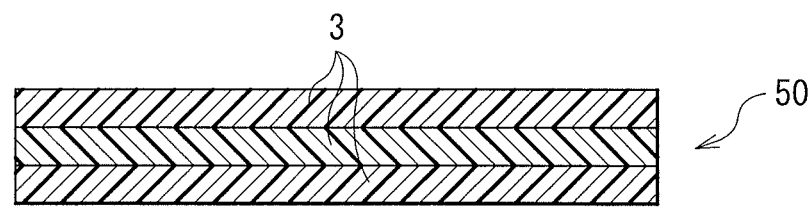

[ FIG. 6 ]
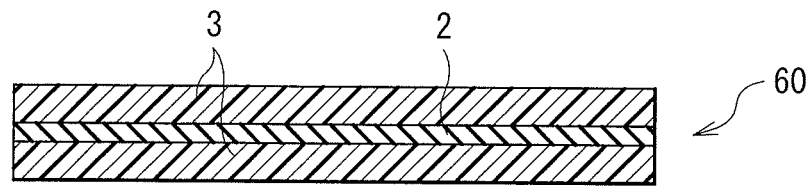
[ FIG. 7 ]
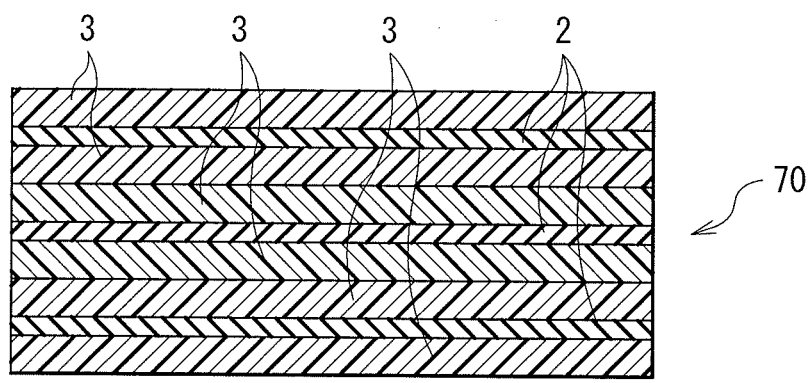
[ FIG. 8 ]
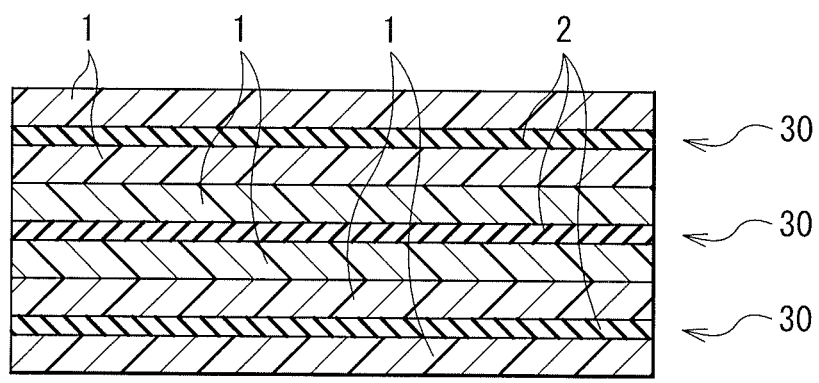

RESIN COMPOSITION, RESIN SHEET, RESIN CURED PRODUCT, AND RESIN SUBSTRATE

TECHNICAL FIELD

The invention relates to a resin composition including an epoxy compound, and to a resin sheet, a resin cured product, and a resin substrate in each of which the resin composition is used.

BACKGROUND ART

There has been a trend toward wide use of various electronic components for high-temperature environment applications such as automobiles. Research and development have been performed actively on thermal characteristics of a resin substrate used for the electronic components, accordingly.

In a manufacturing process of the resin substrate, a resin composition is shaped into a sheet shape, following which the sheet-shaped resin composition (a resin sheet) is subjected to a curing reaction. This results in manufacturing of the resin substrate that includes a cured reactant (a resin cured product) of the resin composition.

Various proposals have been already made on, for example, a composition of the resin composition. Specifically, an epoxy resin having a mesogenic group has been used as a monomer in order to obtain a superior heat-conducting property (for example, see Patent Literature 1).

CITATION LIST

Patent Literature

Patent Literature 1: Japanese Unexamined Patent Application Publication No. H11-323162

SUMMARY OF INVENTION

To examine thermal characteristics of each of a resin composition and a resin substrate (a resin cured product), it is important to take into consideration not only a thermal characteristic, etc., of a resin substrate, but also formability in order to manufacture the resin substrate with use of the resin composition.

What is therefore desired is to provide a resin composition, a resin sheet, a resin cured product, and a resin substrate that are able to achieve a superior thermal characteristic.

A resin composition according to one embodiment of the invention includes an epoxy compound, a first triphenylbenzene compound expressed by the following expression (1), and a second triphenylbenzene compound expressed by the following expression (2), and a ratio M (mol %) expressed by the following mathematical expression (A) is from 0.2 mol % to 16.3 mol %.

[Chemical Formula 1]

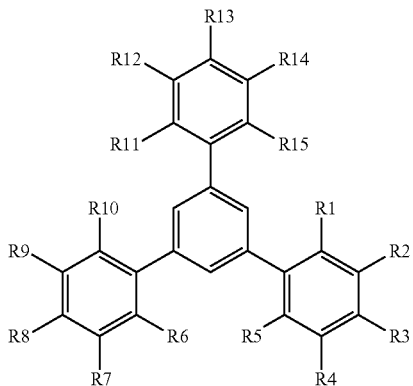

(1)

(R1 to R15 are each any of a hydrogen group (—H) and a hydroxyl group (—OH), where at least one of R1 to R15 is the hydroxyl group.)

[Chemical Formula 2]

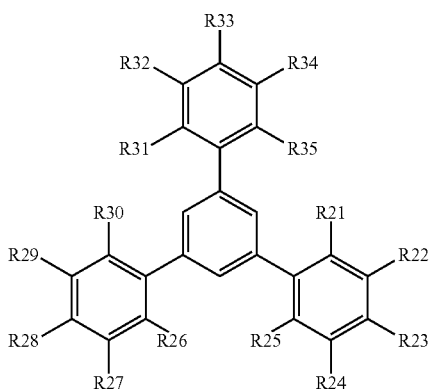

(2)

(R21 to R35 are each any of the hydrogen group, the hydroxyl group, and an alkoxy group, where at least one of R21 to R35 is the hydroxyl group and at least one of R21 to R35 is the alkoxy group.)

$$M(\text{mol \%}) = (M1/M2) \times 100 \quad \text{(A)}$$

M1: the number of moles (mol) of the alkoxy group contained in the second triphenylbenzene compound M2: sum of the number of moles (mol) of the hydroxyl group contained in the first triphenylbenzene compound, the number of moles (mol) of the hydroxyl group contained in the second triphenylbenzene compound, and the number of moles (mol) of the alkoxy group contained in the second triphenylbenzene compound A resin sheet according to one embodiment of the invention includes the resin composition according to one embodiment of the invention described above.

A resin cured product according to one embodiment of the invention includes a cured reactant of the resin composition according to one embodiment of the invention described above.

A resin substrate according to one embodiment of the invention includes the cured reactant according to one embodiment of the resin sheet of the invention described above.

Here, the "hydroxyl group" contained in each of the first triphenylbenzene compound and the second triphenylbenzene compound is a group (a reactive group) that progresses a reaction (a cross-linking reaction) of the epoxy compound with the first triphenylbenzene compound and with the second triphenylbenzene compound. In contrast, the "alkoxy group" contained in the second triphenylbenzene compound is a group (a reaction-adjusting group) that adjusts a reaction speed of the above-described reaction of the epoxy compound with the first triphenylbenzene compound and with the second triphenylbenzene compound. The wording "adjusts the reaction speed" means to intentionally slow down the speed of the reaction to prevent the reaction from progressing rapidly.

The resin composition according to one embodiment of the invention includes the epoxy compound, the first triphenylbenzene compound expressed by the expression (1), and the second triphenylbenzene compound expressed by the expression (2), and the ratio M expressed by the mathematical expression (A) is from 0.2 mol % to 16.3 mol %. Hence, it is possible to achieve a superior thermal characteristic. It is also possible for the resin sheet, the resin cured product, and the resin substrate, each according to one embodiment of the invention, to achieve a similar effect.

BRIEF DESCRIPTION OF DRAWINGS

FIG. 1 is a cross-sectional view of a configuration of a resin sheet in which a resin composition according to the invention is used.

FIG. 2 is a cross-sectional view of another configuration of the resin sheet in which the resin composition according to the invention is used.

FIG. 3 is a cross-sectional view of yet another configuration of the resin sheet in which the resin composition according to the invention is used.

FIG. 4 is a cross-sectional view of a configuration of a resin substrate in which a resin cured product according to the invention is used.

FIG. 5 is a cross-sectional view of another configuration of the resin substrate in which the resin cured product according to the invention is used.

FIG. 6 is a cross-sectional view of yet another configuration of the resin substrate in which the resin cured product according to the invention is used.

FIG. 7 is a cross-sectional view of yet another configuration of the resin substrate in which the resin cured product according to the invention is used.

FIG. 8 is an explanatory cross-sectional view of a method of manufacturing the resin substrate illustrated in FIG. 7.

DESCRIPTION OF EMBODIMENTS

In the following, one embodiment of the invention is described in detail with reference to the drawings. Note that the order of description is as follows.
1. Resin Composition
   1-1. Configuration
   1-2. Manufacturing Method
   1-3. Action and Effect
2. Resin Sheet
   2-1. Configuration
   2-2. Manufacturing Method
   2-3. Action and Effect
3. Resin Cured Product
   3-1. Configuration
   3-2. Manufacturing Method
   3-3. Action and Effect
4. Resin Substrate
   4-1. Configuration
   4-2. Manufacturing Method
   4-3. Action and Effect One embodiment of the invention to be described in the following is an illustrative example for purpose of describing the invention. The invention is therefore not limited only to one embodiment to be described herein. It is possible to alter one embodiment of the invention to any of various embodiments so long as they remain within the scope of the invention.

<1. Resin Composition>

First, a description is given of a resin composition according to one embodiment of the invention.

The resin composition is used for manufacturing of, for example, a resin sheet, a resin cured product, and a resin substrate to be described later. The use of the resin composition, however, may be any other use.

<1-1. Configuration>

The resin composition includes an epoxy compound, a first triphenylbenzene compound expressed by the following expression (1), and a second triphenylbenzene compound expressed by the following expression (2).

[Chemical Formula 3]

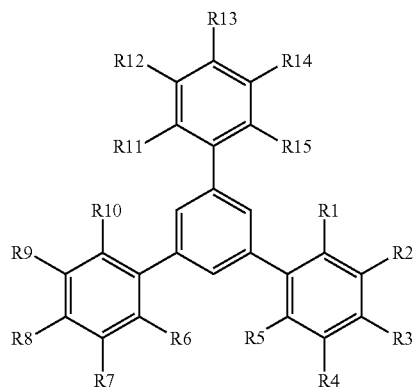

(1)

(R1 to R15 are each any of a hydrogen group and a hydroxyl group, where at least one of R1 to R15 is the hydroxyl group.)

[Chemical Formula 4]

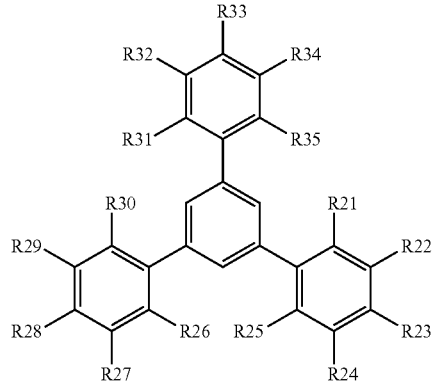

(2)

(R21 to R35 are each any of the hydrogen group, the hydroxyl group, and an alkoxy group, where at least one of R21 to R35 is the hydroxyl group and at least one of R21 to R35 is the alkoxy group.)

As described above, the resin composition to be described here is used to manufacture an intermediate product such as the resin sheet and to manufacture a final product (resin cured product) such as the resin substrate. The term "intermediate product" refers to a material that is in a state in which a curing reaction (a cross-linking reaction) of the resin composition has not substantially been completed as described later. In addition, the term "final product" refers to a material that is in a state in which the curing reaction of the resin composition has substantially been completed as described later.

The epoxy compound, which is a thermosetting resin, is a so-called main agent. On the other hand, the first triphenylbenzene compound, to be used together with the epoxy compound and including a reactive group (hydroxyl group), is a first curing agent that progresses the cross-linking reaction of the epoxy compound with use of the reactive group as described above. Further, the second triphenylbenzene compound, to be used together with the epoxy compound and including the reactive group (hydroxyl group) and a reaction-adjusting group (alkoxy group), is a second curing agent that adjusts a speed of the cross-linking reaction of the epoxy compound with use of the reaction-adjusting group (intentionally slows down the speed of the cross-linking reaction) while progressing the cross-linking reaction of the epoxy compound with use of the reactive group as described above.

A reason why the resin composition includes the first triphenylbenzene compound and the second triphenylbenzene compound together with the epoxy compound is that formability of the resin cured product improves while ensuring a heat-conducting property of the resin cured product.

More specifically, using the first triphenylbenzene compound, including a skeleton having superior heat-conducting property (1, 3, 5-triphenylbenzene) and the reactive group that progresses the cross-linking reaction, results in manufacturing of the resin cured product with use of the resin composition and increases the heat-conducting property of the resin cured product.

In this case, using, together with the above-described first triphenylbenzene compound, the second triphenylbenzene compound, including the reactive group that progresses the cross-linking reaction and the reaction-adjusting group that adjusts the speed of the cross-linking reaction, suppresses the number of reaction points (cross-linking points) such that they do not become too many. In this case, the curing reaction speed upon the curing reaction is suppressed such that the curing reaction speed does not become too fast, and a melt viscosity of the resin composition also decreases accordingly. This makes it easier to maintain a flow state of the resin composition even upon the curing reaction and thereby makes it easier to shape the resin cured product thereof.

In particular, the second triphenylbenzene compound includes a skeleton (1, 3, 5-triphenylbenzene) that is similar to the skeleton of the first triphenylbenzene compound. In this case, it is possible to achieve superior heat-conducting property for the skeleton contained in the second triphenylbenzene compound as well, as with the skeleton contained in the first triphenylbenzene compound. Thus, the formability of the resin cured product increases without decreasing the heat-conducting property even by the combined use of the first triphenylbenzene compound and the second triphenylbenzene compound.

Note, however, that a ratio M (mol %) expressed by the following mathematical expression (A) is from 0.2 mol % to 16.3 mol %.

$$M(\text{mol \%}) = (M1/M2) \times 100 \tag{A}$$

M1: the number of moles (mol) of the alkoxy group contained in the second triphenylbenzene compound M2: sum of the number of moles (mol) of the hydroxyl group contained in the first triphenylbenzene compound, the number of moles (mol) of the hydroxyl group contained in the second triphenylbenzene compound, and the number of moles (mol) of the alkoxy group contained in the second triphenylbenzene compound A reason why the ratio M, i.e., a ratio of the total number of moles (M1) of the reaction-adjusting group to the sum (M2) of the total number of moles of the reactive group (the hydroxyl group) and the total number of moles of the reaction-adjusting group (the alkoxy group), falls within an above-described range is that a balance is made appropriate between the number of hydroxyl groups that progress the cross-linking reaction and the number of reaction-adjusting groups that adjust the speed of the cross-linking reaction. Thus, the curing reaction speed is suppressed moderately and the melt viscosity of the resin composition is decreased, making it possible to maintain the flow state of the resin composition even upon the curing reaction and to manufacture the resin cured product by utilizing the curing reaction as described above.

More specifically, if the ratio M is less than 0.2 mol %, the number of reaction-adjusting groups is too small, making the speed of the cross-linking reaction not slow enough upon the curing reaction despite using the second triphenylbenzene compound that includes the reaction-adjusting group. In this case, the melt viscosity of the resin composition does not decrease sufficiently and the flow state of the resin composition is not sufficiently maintained accordingly upon the curing reaction. Hence, the heat-conducting property increases but the formability is insufficient.

In addition, if the ratio M is greater than 16.3 mol %, the number of reaction-adjusting groups is too large, making the cross-linking reaction not progress enough upon the curing reaction despite using the first triphenylbenzene compound that includes the reactive group and the second triphenylbenzene compound that includes the reactive group. Hence, the resin composition suffers from insufficient curing reaction, making it difficult to manufacture the resin cured product.

In contrast, when the ratio M (mol %) is from 0.2 mol % to 16.3 mol %, the cross-linking reaction progresses sufficiently upon the curing reaction and the speed of the cross-linking reaction is suppressed such that the speed does not become too fast. In this case, the melt viscosity of the resin composition is decreased sufficiently and the resin composition is subjected to the sufficient curing reaction, making it possible to achieve both the increase in the heat-conducting property and the ensuring of the formability.

In particular, it is preferable that the ratio M be from 0.2 mol % to 5.0 mol %. A reason for this is that the balance between the number of hydroxyl groups that progress the cross-linking reaction and the number of reaction-adjusting groups that adjust the speed of the cross-linking reaction is made more appropriate. Thus, the heat-conducting property is further increased while ensuring the formability.

Here, a procedure for determining the ratio M is as follows, for example.

It is to be noted that, for example, the resin sheet as the above-described intermediate product or the resin cured product (such as the resin substrate) as the above-described final product may be used to determine the ratio M. The resin sheet may be any of resin sheets 10, 20, and 30 to be described later for the kind of the resin sheet, and the resin substrate may be any of resin substrates 40, 50, 60, and 70 to be described later for the kind of the resin substrate. In the following, a description is given by referring to an example of the resin cured product.

(Procedure 1)

First, a resin cured product is manufactured with sole use of the first triphenylbenzene compound as a curing agent, following which a reaction reagent is added to the resin cured product. Thereafter, the resin cured product is subjected to rapid heating (temperature=445° C. and time=6 seconds) with use of a pyrolyzer (a Curie point pyrolyzer JHP-5 available from Japan Analytical Industry Co., Ltd.). This results in pyrolysis of the resin cured product and allows a pyrolysis reaction product to be obtained accordingly. The pyrolysis reaction product is a compound in which a reactant of the epoxy compound and the first triphenylbenzene compound is dissociated. Thereafter, the pyrolysis reaction product is subjected to mass spectrometry with use of a gas chromatography mass spectrometer (GCMS-QP5050A available from Shimadzu Corporation). In this case, a column temperature is raised from 40° C. to 320° C. at a rate of temperature rise of 10° C./minute, following which the column temperature is held at 320° C. as it is for 15 minutes. This allows for confirmation of a holding time of a reaction product derived from the first triphenylbenzene compound.

(Procedure 2)

Next, a procedure that is similar to the above-described procedure 1, with exception that the second triphenylbenzene compound is used as the curing agent instead of the first triphenylbenzene compound, is used to manufacture a resin cured product and to confirm a holding time of a reaction product derived from the second triphenylbenzene compound.

(Procedure 3)

Next, the first triphenylbenzene compound is solely used as the curing agent to manufacture a plurality of resin cured products that are different from each other in content of the first triphenylbenzene compound. Thereafter, a procedure that is similar to the above-described procedure 1, with exception that the plurality of resin cured products are used, is used to confirm a holding time of reaction products derived from the first triphenylbenzene compound. On the basis of a result of the confirmation, a calibration curve related to peak area of the reaction product is created.

(Procedure 4)

Next, a procedure that is similar to the above-described procedure 1, with exception that the first triphenylbenzene compound and the second triphenylbenzene compound are used as the curing agents, is used to manufacture a resin cured product and to thereafter confirm a holding time of a reaction product derived from the first triphenylbenzene compound and a holding time of a reaction product derived from the second triphenylbenzene compound. The resin cured product fabricated here is a sample by which the ratio M is to be determined (hereinafter, simply referred to as "sample").

Thereafter, a rate of abundance between the first triphenylbenzene compound and the second triphenylbenzene compound in the sample is calculated from a rate among peak area during the holding time confirmed by the procedure 1, peak area during the holding time confirmed by the procedure 2, and peak area during the holding time confirmed by the procedure 4.

Thereafter, the content of the first triphenylbenzene compound in the sample is calculated with use of the calibration curve created by the procedure 3. Thereafter, the number of moles (mol) of the hydroxyl group contained in the first triphenylbenzene compound as well as the number of moles (mol) of the hydroxyl group and the number of moles (mol) of the alkoxy group contained in the second triphenylbenzene compound are calculated on the basis of the number of hydroxyl groups contained in the first triphenylbenzene compound, the number of hydroxyl groups and the number of alkoxy groups contained in the second triphenylbenzene compound, the rate of abundance between the first triphenylbenzene compound and the second triphenylbenzene compound, and the content of the first triphenylbenzene compound in the sample. Thereafter, the sum M2 (mol) of these numbers of moles is determined.

(Procedure 5)

Finally, the ratio M (mol %) is calculated with use of the mathematical expression (A), on the basis of the number of moles M1 (mol) of the alkoxy group contained in the second triphenylbenzene compound and the above-described sum M2 of the numbers of moles (mol).

The resin composition may be in a solid state such as a powder state and a massive state, may be in a liquid state, or may be in a state in which both of them are mixed. A state of the resin composition is determined as appropriate depending on use, for example.

Note that a rate of mixture among the epoxy compound, the first triphenylbenzene compound, and the second triphenylbenzene compound is not particularly limited. In general, however, a single epoxy group and a single active hydrogen in a reactive group react with each other in a case where the epoxy compound including the epoxy groups and the first triphenylbenzene compound including the reactive groups are subjected to the cross-linking reaction. Such a reaction of a single epoxy group and a single active hydrogen in a reactive group also applies similarly to the second triphenylbenzene compound including the reactive groups. Hence, in order to increase an efficiency of reaction of the epoxy compound with the first triphenylbenzene compound and with the second triphenylbenzene compound, it is preferable that the rate of mixture be set such that the total number of epoxy groups contained in the epoxy compound and the total number of active hydrogen contained in each of the first triphenylbenzene compound and the second triphenylbenzene compound becomes 1:1.

[Epoxy Compound]

The epoxy compound as the main agent is any kind or two or more kinds of compounds containing one or more epoxy groups ($-C_3H_5O$) in a single molecule. In particular, it is preferable that the epoxy compound contain two or more epoxy groups in a single molecule. A reason for this is that this makes it easier for the epoxy compound and the first triphenylbenzene compound to react with each other, and makes it easier for the epoxy compound and the second triphenylbenzene compound to react with each other.

Examples of the epoxy compound include a glycidyl ether type epoxy compound, a glycidyl ester type epoxy compound, a glycidyl amine type epoxy compound, a novolac type epoxy compound, a cycloaliphatic type epoxy compound, and a long-chain aliphatic type epoxy compound, although the epoxy compound is not particularly limited in kind.

Examples of the glycidyl ether type epoxy compound include a bisphenol A type epoxy compound and a bisphenol F type epoxy compound. Examples of the novolac type epoxy compound include a cresol novolac type epoxy compound and a phenol novolac type epoxy compound. Beside these, examples of the kind of the epoxy compound may include a fire-retardant epoxy compound, a hydantoin-based epoxy compound, and an isocyanurate-based epoxy compound.

Note that specific examples of the glycidyl ether type epoxy compound are not particularly limited as long as a compound includes a glycidyl ether type structure (group). A fact that no limitation is made to the kind as long as a particular structure is included as described above also applies similarly to specific examples of other epoxy compounds such as the glycidyl ester type epoxy compound.

In particular, it is preferable that the epoxy compound contain a mesogenic skeleton in a single molecule. A reason for this is as follows.

Firstly, this makes it easier for benzene rings to be overlapped with each other between molecules of the epoxy compound and thereby makes a distance between the benzene rings small. Hence, a density of the epoxy compound increases in the resin composition. Further, lattice vibration of a molecule becomes difficult to scatter in the resin cured product and high thermal conductivity is achieved accordingly.

In particular, the above-described scattering phenomenon of the lattice vibration of the molecule constitutes a major cause of a decrease in thermal conductivity. Hence, the decrease in the thermal conductivity is suppressed significantly by suppressing the scattering phenomenon of the lattice vibration of the molecule.

Secondly, this makes it easier for a benzene ring included in the mesogenic skeleton of the epoxy compound and a benzene ring included in the skeleton (1, 3, 5-triphenylbenzene) of the first triphenylbenzene compound to be overlapped with each other in the epoxy compound and the first triphenylbenzene compound. A fact that the benzene rings become overlapped with each other easily as described above also applies similarly to the epoxy compound and the second triphenylbenzene compound. Hence, high thermal conductivity is achieved owing to a reason similar to that of a case where the benzene rings become overlapped with each other easily between the molecules of the epoxy compound as described above.

The term "mesogenic skeleton" is a generic term for a group of atoms including two or more aromatic rings and having rigidity and orientation. Specifically, the mesogenic skeleton is, for example, a skeleton including two or more benzene rings and in which the benzene rings are bonded to each other through either a single bond or a non-single bond.

Note that a direction of bond in a case where three or more benzene rings are bonded is not particularly limited. In other words, three or more benzene rings may be bonded linearly, may be so bonded as to be bent once or more times along the way, or may be so bonded as to be branched in two or more directions.

The term "non-single bond" is a generic term for a divalent group including one or two or more constituent elements and including one or two or more multiple bonds. Specifically, the non-single bond includes any kind or two or more kinds of constituent elements such as carbon (C), nitrogen (N), oxygen (O), and hydrogen (H). Further, the non-single bond includes one or both of double bond and triple bond as the multiple bond.

The mesogenic skeleton may include only the single bond, only the non-single bond, or both of the single bond and the non-single bond, as the kind of bond between the benzene rings. Further, there may be only one kind or two or more kinds for the kind of the non-single bond.

Specific examples of the non-single bond include those represented by the respective expressions (3-1) to (3-10) as listed below. Note that an arrow illustrated in each of the expressions (3-6) and (3-10) denotes a coordinate bond.

[Chemical Formula 5]

 (3-1)

 (3-2)

 (3-3)

 (3-4)

 (3-5)

 (3-6)

 (3-7)

 (3-8)

 (3-9)

 (3-10)

Specific examples of the mesogenic skeleton include biphenyl and terphenyl. Note that terphenyl may be o-terphenyl, m-terphenyl, or p-terphenyl.

[First Triphenylbenzene Compound]

The first triphenylbenzene compound as the first curing agent is any kind or two or more kinds of compounds including the skeleton (1, 3, 5-triphenylbenzene) and the reactive group (the hydroxyl group). In other words, the first triphenylbenzene compound includes 1, 3, 5-triphenylbenzene in a single molecule as the skeleton, and includes the hydroxyl group introduced in the skeleton.

The skeleton (1, 3, 5-triphenylbenzene) includes a single benzene ring (a center benzene ring) located at the center and three benzene rings (peripheral benzene rings) located around the center benzene ring.

In the following, the peripheral benzene ring in which R1 to R5 are introduced is referred to as a "first peripheral benzene ring", the peripheral benzene ring in which R6 to R10 are introduced is referred to as a "second peripheral benzene ring", and the peripheral benzene ring in which R11 to R15 are introduced is referred to as a "third peripheral benzene ring". These also apply similarly to the second triphenylbenzene compound to be described later.

R1 to R15 are each not particularly limited in kind as long as they are each any of the hydrogen group and the hydroxyl group. In other words, R1 to R15 each may be the hydrogen group or may be the hydroxyl group.

Note, however, that one or more of R1 to R15 is the hydroxyl group. A reason for this is that it is necessary for the first triphenylbenzene compound to include one or more hydroxyl groups in order for the first triphenylbenzene compound to make the cross-linking reaction progress with use of the reactive group (the hydroxyl group). As long as this condition is satisfied, the number of hydroxyl groups, a position of introduction, and so forth are not particularly limited. In particular, it is preferable that two or more of R1 to R15 be the hydroxyl groups. A reason for this is that this makes the epoxy compound and the first triphenylbenzene compound react with each other easily.

In particular, it is preferable that one or both of the following conditions be further satisfied for the kinds of R1 to R15.

A first condition is that, preferably, one or more of R1 to R5 is the hydroxyl group, one or more of R6 to R10 is the hydroxyl group, and one or more of R11 to R15 is the hydroxyl group. A reason for this is that, even when the total number of hydroxyl groups is three or more, the positions at which the respective three or more hydroxyl groups are introduced are dispersed to the respective first to third peripheral benzene rings and thus the epoxy compound and the first triphenylbenzene compound react with each other easily.

In this case, as long as one or more of R1 to R5 is the hydroxyl group, a position at which the one or more hydroxyl groups is introduced in the first peripheral benzene ring is not particularly limited. A fact that the position of introduction of the one or more hydroxyl groups is not limited in a case where the number of hydroxyl groups is one or more also applies similarly to a position at which the one or more hydroxyl groups is introduced in the second peripheral benzene ring, and also applies similarly to a position at which the one or more hydroxyl groups is introduced in the third peripheral benzene ring.

A second condition is that, preferably, one of R1 to R5 is the hydroxyl group, one of R6 to R10 is the hydroxyl group, and one of R11 to R15 is the hydroxyl group. A reason for this is that, in a case where the total number of hydroxyl groups is three, the positions at which the respective three hydroxyl groups are introduced are dispersed to the respective first to third peripheral benzene rings and thus the epoxy compound and the first triphenylbenzene compound react with each other easily.

In this case, as long as one of R1 to R5 is the hydroxyl group, a position at which that one hydroxyl group is introduced in the first peripheral benzene ring is not particularly limited. A fact that the position of introduction of the one hydroxyl group is not limited in a case where the number of hydroxyl groups is one also applies similarly to a position at which the one hydroxyl group is introduced in the second peripheral benzene ring, and also applies similarly to a position at which the one hydroxyl group is introduced in the third peripheral benzene ring.

Specific examples of the first triphenylbenzene compound include compounds expressed by the following respective expressions (1-1) and (1-2). The number of hydroxyl groups is three in the compound expressed by the expression (1-1), and the number of hydroxyl groups is six in the compound expressed by the expression (1-2).

[Chemical Formula 6]

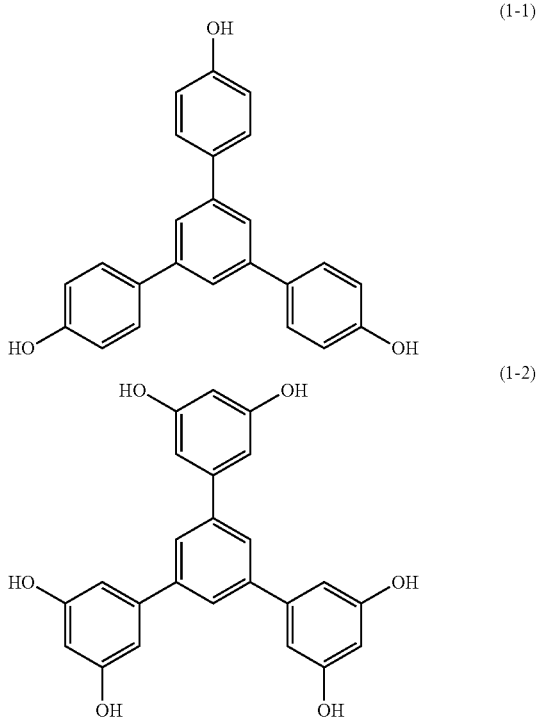

In particular, the compound expressed by the expression (1-1) is preferable. A reason for this is that this satisfies the first and the second conditions described above.

[Second Triphenylbenzene Compound]

The second triphenylbenzene compound as the second curing agent is any kind or two or more kinds of compounds including the skeleton (1, 3, 5-triphenylbenzene), the reactive group (the hydroxyl group), and the reaction-adjusting group (the alkoxy group). In other words, the second triphenylbenzene compound includes 1, 3, 5-triphenylbenzene in a single molecule as the skeleton, and includes the hydroxyl group and the alkoxy group that are introduced in the skeleton.

The first triphenylbenzene compound includes the reactive group (the hydroxyl group) as described above, but includes no reaction-adjusting group (alkoxy group). In contrast, the second triphenylbenzene compound includes the reactive group (the hydroxyl group) as well as the reaction-adjusting group (the alkoxy group).

R21 to R35 are each not particularly limited in kind as long as they are each any of the hydrogen group, the hydroxyl group, and the alkoxy group. In other words, R21 to R35 each may be the hydrogen group, may be the hydroxyl group, or may be the alkoxy group. Note that, in a case where the second triphenylbenzene compound includes a plurality of alkoxy groups, the kinds of the alkoxy groups may be the same as each other, or may be different from each other. It is a matter of course that some of the alkoxy groups may be the same in kind as each other.

The alkoxy group as the reaction-adjusting group serves to suppress the number of reaction points (cross-linking points) such that they do not become too many in order to prevent the cross-linking reaction from becoming too fast upon the curing reaction as described above.

Specific examples of the alkoxy group include a methoxy group ($-OCH_3$), an ethoxy group ($-OC_2H_5$), and a propoxy group ($-OC_3H_7$). The alkoxy group may also be a group other than those described previously. In particular, the methoxy group and the ethoxy group are preferable. A reason for this is that this makes the second triphenylbenzene compound synthesizable easily and allows the reaction-adjusting group to exert its function sufficiently. Note that a propyl group (—$C_3H_7$) in the propoxy group may be a normal propyl group (—$CH_2CH_2CH_3$), or may be an isopropyl group (—$CH(CH_3)_2$).

Note, however, that one or more of R21 to R35 is the hydroxyl group. A reason for this is that it is necessary for the second triphenylbenzene compound to include one or more hydroxyl groups in order for the second triphenylbenzene compound to make the cross-linking reaction progress with use of the hydroxyl group. As long as this condition is satisfied, the number of hydroxyl groups, a position of introduction, and so forth are not particularly limited.

In addition, one or more of R21 to R35 is the alkoxy group. A reason for this is that it is necessary for the second triphenylbenzene compound to include one or more alkoxy groups in order for the second triphenylbenzene compound to adjust the speed of the cross-linking reaction with use of the alkoxy group. As long as this condition is satisfied, the number of alkoxy groups, a position of introduction, and so forth are not particularly limited.

In particular, it is preferable that one or two or more of the following three conditions be satisfied for the kinds of R21 to R35.

A third condition is that, preferably, one of R21 to R25 is the alkoxy group, and respective R26 to R35 are the hydrogen group and the hydroxyl group. In other words, among the first to the third peripheral benzene rings, it is preferable that the alkoxy group be introduced in one peripheral benzene ring and that no alkoxy group be introduced in the remaining two peripheral benzene rings. A reason for this is that this prevents the speed of the cross-linking reaction from decreasing excessively owing to use of the least number of alkoxy groups.

A fourth condition is that, preferably, one of R21 to R25 is the alkoxy group, one of R26 to R30 is the alkoxy group, and R31 to R35 are each any of the hydrogen group and the hydroxyl group. In other words, among the first to the third peripheral benzene rings, it is preferable that one alkoxy group be introduced in each of the two peripheral benzene rings and that no alkoxy group be introduced in the remaining one peripheral benzene ring. A reason for this is that, in a case where the number of alkoxy groups is two, not only the positions at which the respective two alkoxy groups are introduced are dispersed to the respective two peripheral benzene rings and thus steric hindrance of the alkoxy group becomes difficult to occur, but also the number of hydroxyl groups is not too large and thus the speed of the cross-linking reaction becomes sufficiently slow even with the low content of the second triphenylbenzene compound.

A fifth condition is that, preferably, sum of the number of hydroxyl groups and the number of alkoxy groups is three in the second triphenylbenzene compound (a single molecule). In other words, in consideration of the number of hydroxyl groups which is one or more and the number of alkoxy groups which is one or more, it is preferable that the number of hydroxyl groups be one and the number of alkoxy groups be two, or that the number of hydroxyl groups be two and the number of alkoxy groups be one. A reason for this is that this ensures the least number of hydroxyl groups and the least number of alkoxy groups upon achieving both the progress in the cross-linking reaction and the adjustment of the speed of the cross-linking reaction.

Specific examples of the second triphenylbenzene compound include compounds expressed by the following respective expressions (2-1) and (2-6). A reason for this is that the compounds expressed by the respective expressions (2-1), (2-3), and (2-5) satisfy the third and the fifth conditions described above, and that the compounds expressed by the respective expressions (2-2), (2-4), and (2-6) satisfy the fourth and the fifth conditions described above. Note that the number of alkoxy groups is one in the compounds expressed by the respective expressions (2-1), (2-3), and (2-5). The number of alkoxy groups is two in the compounds expressed by the respective expressions (2-2), (2-4), and (2-6). In particular, it is preferable that the second triphenylbenzene compound be any of the compounds expressed by the respective expressions (2-1) to (2-4), in consideration of the alkoxy group for which the methoxy group and the ethoxy group are preferable as described above.

[Chemical Formula 7]

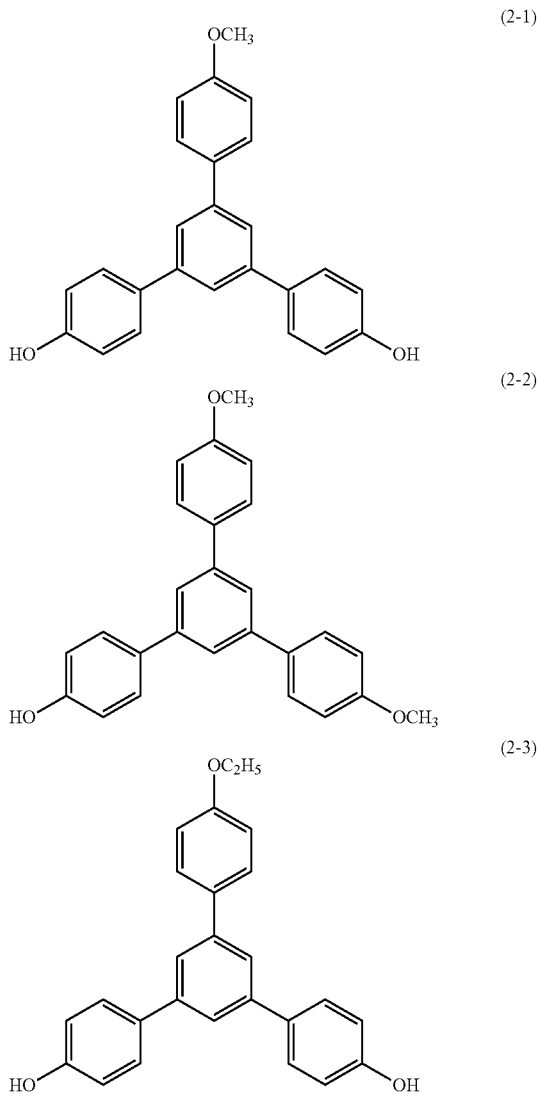

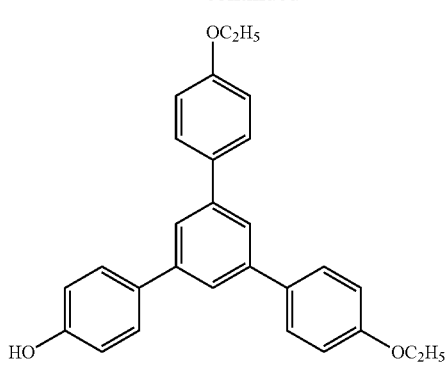

(2-4)

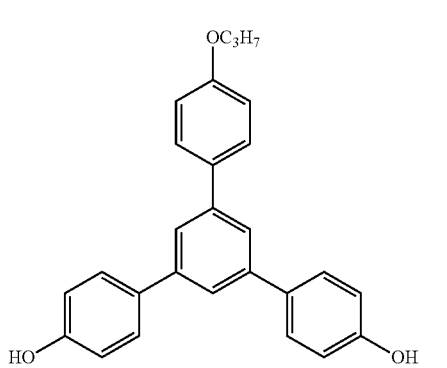

(2-5)

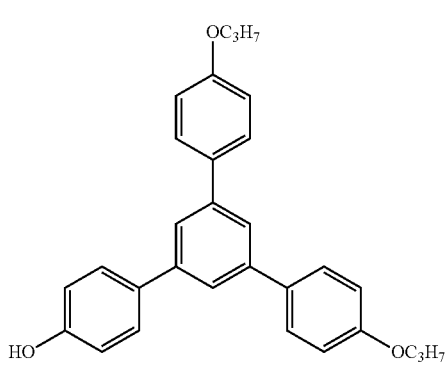

(2-6)

Note that each of the expression (2-1) to the expression (2-6) illustrates a case where, in each of the peripheral benzene rings, the hydroxyl group and the alkoxy group are each introduced at a p-position. However, a position at which each of the hydroxyl group and the alkoxy group is introduced in each of the peripheral benzene rings is not limited to the p-position, and may be an o-position, or may be an m-position.

[Other Materials]

The resin composition may include any kind or two or more kinds of other materials together with the epoxy compound, the first triphenylbenzene compound, and the second triphenylbenzene compound that are described above.

Examples of other materials include an additive, a solvent, any other curing agent, and inorganic particle, although the kinds of other materials are not particularly limited.

Examples of the additive include a curing catalyst and a coupling agent. Specific examples of the curing catalyst include phosphine, imidazole, and their derivatives. Examples of the derivative of the imidazole include 2-ethyl-4-methylimidazole. Specific examples of the coupling agent include a silane coupling agent and a titanate coupling agent.

The solvent is used to disperse or dissolve the epoxy compound, the first triphenylbenzene compound, and the second triphenylbenzene compound in the liquid-state resin composition. The solvent is any kind or two or more kinds of organic solvents. Specific examples of the organic solvent include methyl ethyl ketone, methyl cellosolve, methyl isobutyl ketone, dimethylformamide, propylene glycol monomethylether, toluene, xylene, acetone, 1,3-dioxolane, N-methylpyrrolidone, and γ-butyrolactone.

Any other curing agent is a compound that does not include 1, 3, 5-triphenylbenzene but includes one or more reactive groups. The reactive group described here is one or both of the hydroxyl group and an amino group. Specific examples of any other curing agent include phenol, amine, and acid anhydride.

The inorganic particle is any kind or two or more kinds of particulate inorganic materials. Specific examples of the inorganic particle include a magnesium oxide (MgO), an aluminum oxide ($Al_2O_3$), and a boron nitride (BN).

<1-2. Manufacturing Method>

For example, the resin composition is manufactured through the following procedure.

In a case where the solid resin composition is to be obtained, the epoxy compound, the first triphenylbenzene compound, and the second triphenylbenzene compound are mixed. The epoxy compound may be crushed before the mixing in a case where the epoxy compound in, for example, the massive state is to be used. A fact that the crushing may be performed before the mixing also applies similarly to the first triphenylbenzene compound and the second triphenylbenzene compound. This obtains the solid resin composition that includes the epoxy compound, the first triphenylbenzene compound, and the second triphenylbenzene compound.

It is to be noted that the resin composition may be shaped on an as-necessary basis with use of, for example, a mold after the solid resin composition is obtained.

In a case where the liquid resin composition is to be obtained, the above-described mixture of the epoxy compound, the first triphenylbenzene compound, and the second triphenylbenzene compound is added with a solvent, following which the solvent is stirred with use of a stirring device such as a mixer. This disperses or dissolves the epoxy compound, the first triphenylbenzene compound, and the second triphenylbenzene compound in the solvent. Thus, the liquid resin composition is obtained that includes the epoxy compound, the first triphenylbenzene compound, and the second triphenylbenzene compound.

The solid resin composition may be heated to melt the resin composition in a case where the liquid resin composition is to be obtained alternatively. In this case, the molten material of the resin composition may be shaped on an as-necessary basis with use of, for example, a mold followed by cooling of the molten material.

Note that a compound in a solid state such as a powder state and a massive state, a compound in a liquid state, or a combination of both of them may be used as the epoxy compound. Similarly, a compound in a solid state such as a powder state and a massive state, a compound in a liquid state, or a combination of both of them may be used as the curing agent of, for example, each of the first triphenylbenzene compound and the second triphenylbenzene compound. What has been described here also applies similarly to any other material described above.

<1-3. Action and Effect>

The resin composition includes the epoxy compound, the first triphenylbenzene compound expressed by the expression (1), and the second triphenylbenzene compound expressed by the expression (2), and the ratio M is from 0.2 mol % to 16.3 mol %. In this case, the formability of the resin cured product improves while ensuring, for example, the heat-conducting property of the resin cured product as described above. Hence, it is possible to obtain a superior thermal characteristic.

In particular, the heat-conducting property is further increased while ensuring the formability when the ratio M is from 0.2 mol % to 5.0 mol %, making it possible to achieve a higher effect.

Further, the epoxy compound and the first triphenylbenzene compound react with each other easily when one or more of R1 to R5 is the hydroxyl group, one or more of R6 to R10 is the hydroxyl group, and one or more of R11 to R15 is the hydroxyl group in the expression (1), making it possible to achieve a higher effect. In this case, it is possible to achieve an even higher effect when one of R1 to R5 is the hydroxyl group, one of R6 to R10 is the hydroxyl group, and one of R11 to R15 is the hydroxyl group.

Further, it is possible to achieve a higher effect when the first triphenylbenzene compound includes the compound expressed by the expression (1-1).

Further, the epoxy compound and the second triphenylbenzene compound react with each other easily when one of R21 to R25 is the alkoxy group and R26 to R35 are each any of the hydrogen group and the hydroxyl group in the expression (2), making it possible to achieve a higher effect.

Further, the speed of the cross-linking reaction becomes sufficiently slow even with the low content of the second triphenylbenzene compound when one of R21 to R25 is the alkoxy group, one of R26 to R30 is the alkoxy group, and R31 to R35 are each any of the hydrogen group and the hydroxyl group, making it possible to achieve a higher effect especially in terms of the formability.

Further, a higher effect is achieved when the sum of the number of hydroxyl groups and the number of alkoxy groups is three in the second triphenylbenzene compound (a single molecule).

Further, a higher effect is achieved when the second triphenylbenzene compound includes any kind or two or more kinds of the compounds expressed by the respective expressions (2-1) and (2-6). In particular, an even higher effect is achieved when the second triphenylbenzene compound includes any kind or two or more kinds of the compounds expressed by the respective expressions (2-1) and (2-4).

It is to be noted that the kind of the reaction-adjusting group is not limited to the foregoing alkoxy group, and is not particularly limited as long as the reaction-adjusting group is a group that is able to suppresses the number of reaction points (cross-linking points) such that they do not become too many upon the curing reaction, i.e., able to suppress the speed of the cross-linking reaction such that speed does not become too fast. The reaction-adjusting group may be a group having no involvement in the cross-linking reaction, i.e., a group that is not used for the reaction of the epoxy compound with the second triphenylbenzene compound.

<2. Resin Sheet>

A description is given next of a resin sheet according to one embodiment of the invention. In the following, the resin composition already described is referred to as a "resin composition of the invention".

The resin sheet includes the resin composition of the invention. A configuration of the resin sheet is not particularly limited as long as the resin sheet includes the resin composition of the invention. In other words, the resin sheet may not be provided with other components together with the resin composition, or may be provided with other components together with the resin composition.

<2-1. Configuration>

FIG. 1 illustrates a cross-sectional configuration of a resin sheet 10. The resin sheet 10 is a resin composition (a resin composition layer 1) shaped into a sheet shape. More specifically, the resin sheet 10 is a monolayer body configured by the single resin composition layer 1. The resin sheet 10 is not particularly limited in thickness, for example. A configuration of the resin composition layer 1 is similar to the configuration of the resin composition of the invention, with exception that the resin composition layer 1 is shaped into the sheet shape.

FIG. 2 illustrates a cross-sectional configuration of a resin sheet 20. The resin sheet 20 is a laminate in which the plurality of resin composition layers 1 are stacked. The number of resin composition layers 1 (the number of stacks) stacked in the resin sheet 20 is not particularly limited as long as the number of layers is two or more. FIG. 2 illustrates a case where the number of stacks of the resin composition layers 1 is three, for example. Note that a configuration of each of the resin composition layers 1 in the resin sheet 20 is not particularly limited. In other words, the configurations of the resin compositions in the respective resin composition layers 1 may be the same as each other, or may be different from each other. It is a matter of course that some resin composition layers 1 of the plurality of resin composition layers 1 may be the same as each other in configuration of the resin composition.

FIG. 3 illustrates a cross-sectional configuration of a resin sheet 30. The resin sheet 30 is provided with a core 2 together with the resin composition (the resin composition layer 1) shaped into the sheet shape. For example, the resin sheet 30 has a three-layer structure in which the core 2 is interposed between the two resin composition layers 1.

The core 2 includes any kind or two or more kinds of materials such as fibrous materials and non-fibrous materials, and is shaped into a sheet shape. Examples of the fibrous material include glass fiber, carbon fiber, metal fiber, natural fiber, and synthetic fiber. Examples of fibrous material shaped into the sheet shape include woven fabric and non-woven fabric. Specific examples of the synthetic fiber include polyester fiber and polyamide fiber. Examples of the non-fibrous material include a polymer compound. Examples of the non-fibrous material shaped into the sheet shape include a polymer film. Specific examples of the polymer compound include polyethylene terephthalate (PET).

It is preferable that a thickness of the core 2 be, for example, from 0.03 mm to 0.2 mm in terms of mechanical strength and dimensional stability, although the core 2 is not particularly limited in thickness.

The resin composition layer 1 to be used for the resin sheet 30 may be solely a single layer, or may be two or more layers. A fact that a single layer or two or more layers suffice as described above also applies similarly to the core 2.

Further, the resin sheet 30 is not limited to the three-layer structure in which the core 2 is interposed between the two resin composition layers 1, and may have a two-layer structure in which the resin composition layer 1 and the core 2 are stacked. Note that two or more resin sheets 20 may be stacked.

<2-2. Manufacturing Method>

For example, a procedure similar to the method of manufacturing the resin composition of the invention is used in a case where the resin sheet 10 is to be manufactured.

Specifically, in a case where the solid resin composition is to be used, the resin composition is so shaped as to be in the sheet shape to thereby form the resin composition layer 1. In this case, the solid resin composition may be shaped as it is, or a molten material of the solid resin composition may be shaped. In a case where the molten material is to be shaped, the solid resin composition is heated to melt the resin composition first. Thereafter, the molten material of the resin composition is shaped followed by cooling of a shaped product.

In a case where the liquid resin composition is to be used, a surface of a support such as a polymer film is applied with the liquid resin composition, following which the liquid resin composition is dried. This volatilizes the solvent contained in the liquid resin composition and thereby results in shaping of the resin composition into the sheet shape on the surface of the support. In other words, the resin composition turns into a film on the surface of the support, thereby forming the resin composition layer 1. Thereafter, the resin composition layer 1 is removed from the support.

The above-described procedure for the formation of the resin composition layer 1 is repeated to stack the plurality of resin composition layers 1 in a case where the resin sheet 20 is to be manufactured. In this case, the laminate may be applied with pressure while performing heating on an as-necessary basis after the formation of the laminate in which the plurality of resin composition layers 1 are stacked. This causes the resin composition layers 1 to be closely attached to each other.

In a case where the resin sheet 30 having the three-layer structure is to be manufactured, both sides of the core 2 are applied with the liquid resin composition, following which the liquid resin composition is dried, for example. This forms the two resin composition layers 1 in such a manner as to interpose the core 2 therebetween. In a process of applying the liquid resin composition, a surface of the core 2 is coated with the liquid resin composition and the inside of the core 2 is impregnated with part of the liquid resin composition in a case where the core 2 includes the fibrous material, or the surface of the core 2 is coated with the liquid resin composition in a case where the core 2 includes the non-fibrous material.

It is a matter of course that only one side of the core 2 may be applied with the liquid resin composition in a case where the resin sheet 30 having the two-layer structure is to be manufactured.

Note that, for example, the solid resin composition is heated to melt the resin composition followed by immersion of the core 2 in the molten material in a case where the resin sheet 30 is to be manufactured. In this case, the core 2 is cooled after the core 2 is taken out from the molten material. This forms the resin composition layer 1 on both sides of the core 2.

Here, the liquid resin composition turns into the film (solidifies) in a drying process as described above in a case where the liquid resin composition is used to manufacture the resin sheets 10, 20, and 30. Note, however, that the wording "turns into the film (solidifies)" as described herein refers to changing of a substance, which is in a state in which the substance has fluidity (a liquid state), to a self-supportable state (a solid state), and encompasses a so-called semi-cured state. In other words, in a case where the liquid resin composition turns into the film, a curing reaction is not completed substantially and thus the resin composition is substantially in an uncured state. Hence, it is preferable that a drying condition upon turning the liquid resin composition into the film be a condition that does not complete the curing reaction substantially. Specifically, it is preferable that a drying temperature be from 60° C. to 150° C. and a drying time be from one minute to 120 minutes, and it is more preferable that the drying temperature be from 70° C. to 120° C. and the drying time be from 3 minutes to 90 minutes.

A fact that the condition is preferable that does not complete the curing reaction substantially also applies similarly to a case where the molten material of the solid resin composition is used to manufacture the resin sheets 10, 20, and 30. In other words, a heating condition (a heating temperature and a heating time) upon melting the solid resin composition is preferably a condition that does not complete the curing reaction substantially.

<2-3. Action and Effect>

The resin sheet includes the above-described resin composition of the invention. Hence, it is possible to obtain the superior thermal characteristic for a reason similar to that of the resin composition. Other actions and effects are similar to those of the resin composition of the invention.

<3. Resin Cured Product>

A description is given next of a resin cured product according to one embodiment of the invention.

<3-1. Configuration>

The resin cured product includes the cured reactant of the above-described resin composition of the invention. More specifically, the resin cured product includes the cured reactant of the epoxy compound as well as the first triphenylbenzene compound and the second triphenylbenzene compound. In the cured reactant, the epoxy group included in the epoxy compound and the hydroxyl group included in each of the first triphenylbenzene compound and the second triphenylbenzene compound have undergone the cross-linking reaction, thus forming a so-called crosslink network.

Note that the resin cured product is not particularly limited in shape. Specifically, the resin cured product may be so shaped as to be in a desired shape, or may not be shaped.

Further, the resin cured product is not particularly limited in property. Specifically, the resin cured product may have quality (rigidity) that makes it difficult for the resin cured product to deform in response to external force, or may have quality (flexibility or plasticity) that makes it easy for the resin cured product to deform in response to the external force.

<3-2. Manufacturing Method>

The resin composition is heated in a case where the resin cured product is to be manufactured. This results in the curing reaction of the resin composition, thereby obtaining the resin cured product as the cured reactant.

A heating condition such as a heating temperature and a heating time is not particularly limited. It is, however, preferable that the condition be a condition that progresses the curing reaction substantially unlike the above-described method of manufacturing the resin sheet.

<3-3. Action and Effect>

The resin cured product includes the cured reactant of the above-described resin composition of the invention. Hence, it is possible to obtain the superior thermal characteristic for a reason similar to that of the resin composition. Other actions and effects are similar to those of the resin composition of the invention.

<4. Resin Substrate>

A description is given next of a resin substrate according to one embodiment of the invention. In the following, the resin sheet and the resin cured product that are already described are respectively referred to as a "resin sheet of the invention" and a "resin cured product of the invention".

The resin substrate is one of application examples of the above-described resin cured product of the invention, and includes the resin cured product of the invention. The resin substrate to be described here includes, for example, the cured reactant of the resin sheet of the invention. A configuration of the resin substrate is not particularly limited as long as the resin substrate includes the cured reactant of the resin sheet of the invention.

Note that what has been described regarding the property of the resin cured product (presence of rigidity) also applies similarly to a property of the resin substrate.

That is, the resin substrate may have rigidity, or may have flexibility or plasticity. This means that, as long as the resin substrate includes the cured reactant of the resin sheet, for example, the resin substrate described here not only encompasses the cured reactant having the rigidity but also the cured reactant having the flexibility or the plasticity. The cured reactant having the flexibility or the plasticity is, for example, an adhesion tape as a sheet-shaped adhesive, or the like.

Further, the number of cured reactants of the resin sheets included in the resin substrate is not particularly limited. In other words, the number of cured reactants of the resin sheets may be only one, or may be two or more. In a case where the number of cured reactants of the resin sheets is two or more, the two or more cured reactants of the resin sheets may be stacked.

<4-1. Configuration>

FIG. 4 illustrates a cross-sectional configuration of a resin substrate 40. The resin substrate 40 is the cured reactant of the resin sheet 10 illustrated in FIG. 1. In other words, the resin substrate 40 is the cured reactant of the resin composition layer 1 (a resin cured product layer 3). More specifically, the resin substrate 40 is a monolayer body configured by the single resin cured product layer 3.

FIG. 5 illustrates a cross-sectional configuration of a resin substrate 50. The resin substrate 50 is the cured reactants of the resin sheets 20 illustrated in FIG. 2. More specifically, the resin substrate 50 is a laminate in which the plurality of cured reactants of the resin composition layers 1 (the resin cured product layers 3) are stacked. The number of resin cured product layers 3 to be stacked (the number of stacks) is not particularly limited as long as the number of layers is two or more. FIG. 5 illustrates a case where the number of stacks of the resin cured product layers 3 is three, for example.

FIG. 6 illustrates a cross-sectional configuration of a resin substrate 60. The resin substrate 60 is the resin cured products of the resin sheets 30 illustrated in FIG. 3. More specifically, the resin substrate 60 has a three-layer structure in which the single core 2 is interposed between the two resin cured product layers 3.

FIG. 7 illustrates a cross-sectional configuration of a resin substrate 70. In the resin substrate 70, two or more cured reactants of the resin sheets 30 are stacked. Here, three cured reactants of the resin sheets 30 are stacked, for example. In other words, the three-layer structure is formed in which the single core 2 is interposed between the two resin cured product layers 3, and three stages of such three-layer structures are laid on top of each other.

Note that the number of above-described three-layer structures to be laid on top of each other (the number of stages) is not limited to three stages, and may be two stages or may be four or more stages. It is possible to set the number of stages as appropriate on the basis of a condition such as a thickness and strength of the resin substrate 70.

The resin substrate 70 may be provided with an unillustrated metal layer. The metal layer is provided on a surface of the uppermost resin cured product layer 3 and on a surface of the lowermost resin cured product layer 3, for example.

The metal layer includes any kind or two or more kinds of copper, nickel, and aluminum, for example. Further, for example, the metal layer includes any kind or two or more kinds of a metal foil and a metal plate. The metal layer may be a monolayer, or may be a multilayer. The metal layer may have a thickness from 3 μm to 150 μm, for example, although the metal layer is not particularly limited in thickness. The resin substrate 70 provided with the metal layer is a so-called metal-clad substrate.

Note that the metal layer may be provided only on the surface of the uppermost resin cured product layer 3, or may be provided only on the surface of the lowermost resin cured product layer 3.

The resin substrate 70 provided with the metal layer may be subjected to any kind or two or more kinds of various processes such as an etching process and a hole making process on an as-necessary basis. In this case, the resin substrate 70, the metal layer having been subjected to the above-described various processes, and any kind or two or more kinds of the resin sheets 10, 20, and 30 may be overlaid with each other to form a multilayer substrate.

A fact that the metal layer may be provided and the multilayer substrate may be formed applies not only to the resin substrate 70 but also to the above-described resin substrates 40, 50, and 60 similarly.

<4-2. Manufacturing Method>

The resin sheet 10 is heated in a case where the resin substrate 40 is to be manufactured. This substantially completes the curing reaction of the resin composition in the resin composition layer 1 as described above, thereby forming the resin cured product layer 3 as the resin cured product of the resin composition layer 1 as illustrated in FIG. 4.

The resin sheet 20 is heated in a case where the resin substrate 50 is to be manufactured. This substantially completes the curing reaction of the resin composition in each of the resin composition layers 1 as described above, thereby forming the plurality of resin cured product layers 3 as the cured reactants of the resin composition layers 1 as illustrated in FIG. 5.

The resin sheet 30 is heated in a case where the resin substrate 60 is to be manufactured. This substantially completes the curing reaction of the resin composition in each of the resin composition layers 1 as described above, thereby forming the resin cured product layer 3 as the cured reactant of the resin composition layer 1 on both sides of the core 2 as illustrated in FIG. 6.

FIG. 8 illustrates a cross-sectional configuration corresponding to FIG. 7 to describe a method of manufacturing the resin substrate 70. In a case where the resin substrate 70 is to be manufactured, the three resin sheets 30 are stacked first as illustrated in FIG. 8. This obtains a laminate of the three resin sheets 30. Thereafter, the laminate is heated. This substantially completes, in each of the resin sheets 30, the curing reaction of the resin composition in each of the resin composition layers 1, thereby forming the resin cured product layer 3 as the cured reactant of the resin composition layer 1 on both sides of each of the cores 2 as illustrated in FIG. 7.

In a case where the molten material of the resin composition is to be used to manufacture the resin sheets 10, 20, and 30, the curing reaction is to be prevented from being completed substantially upon melting of the resin composition. Hence, it is preferable that a temperature that heats the resin composition in order to obtain the molten material be lower than a temperature at which the curing reaction of the resin composition substantially completes. In other words, a melt temperature of the resin composition is preferably lower than the temperature at which the curing reaction of the resin composition substantially completes.

To give one example, in general, a maximum value (a maximum temperature) of a heating temperature upon shaping becomes about 250° C. in a shaping process that uses a mold. Hence, the melt temperature of the resin composition is preferably a temperature that is lower than 250° C., and is more preferably equal to or less than 200° C.

The term "melt temperature" as described herein refers to a temperature at which a state of the resin composition changes from the solid state to the flow (melt) state while the curing reaction of the resin composition is prevented from being completed substantially. In order to identify the melt temperature, a state of the resin composition is observed visually while heating the resin composition with use of a heating apparatus such as a hot plate, for example. In this case, the heating temperature is raised gradually while mixing the resin composition with use of a paddle, for example. A temperature at which the resin composition thus starts to melt is the melt temperature.

In a case where the maximum temperature upon shaping is about 250° C. as described above, the heating temperature upon the shaping is a temperature that is at least 50° C. higher than the melt temperature of the resin composition, specifically from 100° C. to 250° C., and a heating time is about one minute to about 300 minutes, for example. This sufficiently heats the resin composition at the temperature at which the curing reaction substantially completes and thus allows the curing reaction to progress evenly.

Note that, in the shaping process that uses the mold, the resin composition may be applied with pressure with use of a pressing machine or the like where necessary, or a pressure of an environment under which the resin composition is present may be increased or decreased where necessary.

In particular, in a case where the resin substrate 70 is to be manufactured, it is preferable that the laminate be heated while applying the pressure to the laminate in a direction in which the resin sheets 30 are stacked. A reason for this is that this increases, for example, adhesion of the resin sheets 30. One example of a heating condition and a pressure applying condition in this case involves the heating temperature of 100° C. to 250° C., the heating time of one minute to 300 minutes, and the pressure of the pressure application of 0.5 MPa to 8 MPa, although the heating condition and the pressure applying condition are not particularly limited.

<4-3. Action and Effect>

The resin substrate includes the resin cured product of the invention. Hence, it is possible to obtain the superior thermal characteristic for a reason similar to that of the resin cured product. Other actions and effects are similar to those of the resin cured product of the invention.

EXAMPLES

A description is given in detail of Examples of the invention.

Experimental Examples 1 to 20

A resin substrate 50 was manufactured that was configured by the laminate in which the plurality of resin cured product layers 3 were stacked as illustrated in FIG. 5. It is to be noted that the content (pts·mass) to be described hereinafter is a value in solid equivalent.

The epoxy compound, the first curing agent, the second curing agent, and the additive (the curing catalyst) were first mixed for manufacturing the resin substrate 50. In this case, a rate of mixture among the epoxy compound, the first curing agent, and the second curing agent was so adjusted that a ratio between the number of epoxy groups contained in the epoxy compound and the number of active hydrogen contained in each of the first triphenylbenzene compound and the second triphenylbenzene compound becomes 1:1.

The presence, the kind, and the content (pts·mass) in the mixture of each of the epoxy compound, the first curing agent, and the second curing agent are as illustrated in Tables 1 and 2. A biphenyl-type epoxy resin (BER: YL6121H available from Mitsubishi Chemical Corporation) was used as the epoxy compound. The compound expressed by the expression (1-1) and 4,4'-dihydroxy-3-methyl-p-terphenyl (DHMT) were used as the first curing agent. The compounds expressed by the respective expressions (2-1), (2-2), and (2-6) were used as the second curing agent. The presence of "TPB skeleton" illustrated in the Tables 1 and 2 represents whether or not the first curing agent includes 1, 3, 5-triphenylbenzene as the skeleton. As the curing catalyst, 2-ethyl-4-methylimidazole was used. An amount of addition of the curing catalyst was one mass % to the total of the epoxy compound and the curing agents.

In this case, the kind, the content, and so forth of each of the first curing agent and the second curing agent were changed to adjust the ratio M (mol %). The ratio M (mol %) was as illustrated in the Tables 1 and 2.

The mixture was thereafter fed into a solvent (methyl ethyl ketone), following which the solvent was stirred. The amount of addition of the curing catalyst was one mass % to the total of the epoxy compound and the curing agents. This dissolved the epoxy compound, the first curing agent, and the second curing agent in the solvent, and obtained the liquid resin composition accordingly. In this case, the concentration of the solid content (the epoxy compound, the first curing agent, and the second curing agent) was 65 mass %.

Thereafter, a surface of a support (PET film and thickness=0.05 mm) was applied with the liquid resin composition, following which the liquid resin composition was dried (temperature=100° C.). This formed the resin composition layer 1 on the surface of the support, and obtained the resin sheet 10 (thickness=0.1 mm) accordingly as the monolayer body illustrated in FIG. 1. The resin sheet 10 was thereafter removed from the support.

Thereafter, ten sheets of resin sheets 10 were overlaid to fabricate the resin sheet 20 (the number of stacks of the resin composition layers 1=10 layers) as the laminate illustrated in FIG. 2. Finally, the laminate was applied with heat (temperature=170° C.) and pressure (pressure=1 MPa and time=20 minutes) with use of a flat-plate pressing machine, following which the laminate was further applied with heat (temperature)=200° C. and pressure (pressure=4 MPa and time=one hour). In this heating process, the reaction of the resin composition was substantially completed in each of the resin composition layers 1, and thus the resin cured product layers 3 each including the cured reactant of the resin composition were formed. This completed the resin substrate 50 (the number of stacks of the resin cured product layers 3=10 layers and thickness=0.9 mm).

Results illustrated in the Tables 1 and 2 were obtained through examining a thermal characteristic of each of the resin composition, the resin sheet 20 (the resin composition layer 1), and the resin substrate 50 (the resin cured product layer 3). Here, the examination was performed on the formability of the resin composition and the resin sheet 20, and on the heat-conducting property of the resin substrate 50.

To examine the formability, the solid resin composition, i.e., a mixture of the epoxy compound, the first curing agent, the second curing agent, and the curing catalyst, was used to examine the melt temperature (° C.) of the mixture. In this case, on the basis of the above-described procedure, a temperature at which the mixture started to melt while heating the mixture with use of the hot plate was determined as the melt temperature.

Further, to examine the formability, a minimum melt viscosity (mPa·s) of the resin sheet 20 was measured with use of a viscoelasticity measuring apparatus. In this case, the resin sheet 20 was shaped to fabricate a circular measurement sample (diameter=20 mm and thickness=1.8 mm). Thereafter, the measurement sample was heated under conditions of an onset temperature of 100° C., a rate of temperature rise of 2.5° C./minute, and a frequency of 1 Hz to measure the minimum melt viscosity, with use of a viscoelasticity measuring apparatus (Rheo Stress 6000 available from Thermo Fisher Scientific, Inc.). In this case, the viscosity was decreased in accordance with the melting of the measurement sample, following which the viscosity was increased with the progress in the curing reaction, whereby a downward convex-shaped viscosity curve was obtained. A minimum value in the viscosity curve was determined as the minimum melt viscosity.

To examine the heat-conducting property, the thermal conductivity (W/(m·K)) of the resin substrate 50 was measured. Specifically, first, the resin substrate 50 was cut to fabricate a circular measurement sample (diameter=10 mm and thickness=0.9 mm). Thereafter, the measurement sample was analyzed to measure a thermal diffusivity coefficient $\alpha$ ($m^2/s$), with use of a thermal conductivity measuring apparatus (TC series available from Advance Riko, Inc. (former ULVAC-Riko, Inc.)). In addition, specific heat Cp of the measurement sample was measured with use of a differential scanning calorimeter (DSC), where sapphire was used as a reference sample. Further, a density r of the measurement sample was measured with use of the Archimedean method. Finally, the thermal conductivity $\lambda$ (W/(m·K)) was calculated on the basis of the following mathematical expression (B).

$$\lambda = \alpha \times Cp \times r \quad (B)$$

(where $\lambda$ is the thermal conductivity (W/(m·K)), a is the thermal diffusivity coefficient ($m^2/s$), Cp is the specific heat (J/kg·K), and r is the density ($kg/m^3$).)

TABLE 1

| Experimental Examples | Epoxy compound Kind | Content (pts · mass) | First curing agent Kind | TPB skeleton | Content (pts · mass) | Second curing agent Kind | Content (pts · mass) | Ratio M (mol %) | Melt Temp (° C.) | Minimum melt viscosity (mPa · s) | Thermal conductivity (W/(m · K)) |
|---|---|---|---|---|---|---|---|---|---|---|---|
| 1 | BER | 60 | Expression (1-1) | Included | 39.8 | Expression (2-1) | 0.2 | 0.2 | 120 | 540 | 0.33 |
| 2 | BER | 60 | Expression (1-1) | Included | 39.4 | Expression (2-1) | 0.6 | 0.5 | 120 | 520 | 0.33 |
| 3 | BER | 60 | Expression (1-1) | Included | 39 | Expression (2-1) | 1 | 0.8 | 120 | 490 | 0.32 |
| 4 | BER | 60 | Expression (1-1) | Included | 33.8 | Expression (2-1) | 6.2 | 5.0 | 110 | 320 | 0.32 |
| 5 | BER | 60 | Expression (1-1) | Included | 28 | Expression (2-1) | 12 | 9.7 | 100 | 240 | 0.31 |
| 6 | BER | 60 | Expression (1-1) | Included | 20 | Expression (2-1) | 20 | 16.3 | 90 | 180 | 0.31 |
| 7 | BER | 60 | Expression (1-1) | Included | 39 | Expression (2-2) | 1 | 1.5 | 115 | 440 | 0.32 |
| 8 | BER | 60 | Expression (1-1) | Included | 36.5 | Expression (2-2) | 3.5 | 5.1 | 105 | 290 | 0.31 |
| 9 | BER | 60 | Expression (1-1) | Included | 32 | Expression (2-2) | 8 | 12.5 | 90 | 200 | 0.31 |
| 10 | BER | 60 | Expression (1-1) | Included | 30 | Expression (2-2) | 10 | 15.7 | 85 | 115 | 0.31 |
| 11 | BER | 60 | Expression (1-1) | Included | 38 | Expression (2-1) + Expression (2-2) | 1 + 1 | 2.4 | 117 | 430 | 0.32 |
| 12 | BER | 60 | Expression (1-1) | Included | 35.8 | Expression (2-1) + Expression (2-2) | 2 + 2.2 | 5.0 | 105 | 310 | 0.32 |
| 13 | BER | 60 | Expression (1-1) | Included | 30 | Expression (2-1) + Expression (2-2) | 5 + 5 | 11.9 | 95 | 210 | 0.31 |

TABLE 2

| Experimental Examples | Epoxy compound Kind | Content (pts · mass) | First curing agent Kind | TPB skeleton | Content (pts · mass) | Second curing agent Kind | Content (pts · mass) | Ratio M (mol %) | Melt Temp (° C.) | Minimum melt viscosity (mPa · s) | Thermal conductivity (W/(m · K)) |
|---|---|---|---|---|---|---|---|---|---|---|---|
| 14 | BER | 60 | Expression (1-1) | Included | 24 | Expression (2-1) + Expression (2-2) | 12 + 4 | 16.1 | 100 | 160 | 0.31 |
| 15 | BER | 60 | Expression (1-1) | Included | 29 | Expression (2-1) + Expression (2-2) | 2 + 9 | 15.8 | 90 | 110 | 0.31 |
| 16 | BER | 60 | Expression (1-1) | Included | 39 | Expression (2-6) | 1 | 1.4 | 120 | 490 | 0.32 |
| 17 | BER | 60 | Expression (1-1) | Included | 39.9 | Expression (2-1) | 0.1 | 0.1 | 120 | 550 | 0.33 |
| 18 | BER | 60 | Expression (1-1) | Included | 28 | Expression (2-1) + Expression (2-2) | 2 + 10 | 17.4 | 80 | 95 | 0.3 |
| 19 | BER | 60 | Expression (1-1) | Included | 40 | — | — | — | 120 | 550 | 0.33 |
| 20 | BER | 56 | DHMT | Not included | 44 | — | — | — | — | 230 | — |

The melt temperature, the minimum melt viscosity, and the thermal conductivity varied greatly in accordance with the presence, the kind, and so forth of each of the first curing agent and the second curing agent, irrespective of the kind of the epoxy compound.

Specifically, the melt temperature increased significantly in a case where the first curing agent included no TPB skeleton and the second curing agent was unused (Experimental Example 20). In this case, the minimum melt viscosity and the thermal conductivity were not measured by determining that use of the resin composition for shaping purpose is not possible fundamentally due to the melt temperature which was too high.

In a case where the first curing agent included the TPB skeleton but the second curing agent was unused (Experimental Example 19), the melt temperature was sufficiently low and the sufficient thermal conductivity was obtained. The minimum melt viscosity, however, increased significantly.

Cases where the first curing agent included the TPB skeleton and the second curing agent was used (Experimental Examples 1 to 18) showed great disparity in each of the melt temperature, the minimum melt viscosity, and the thermal conductivity in accordance with the ratio M.

Specifically, the melt temperature was sufficiently low and the sufficient thermal conductivity was obtained, but the minimum melt viscosity increased significantly in a case where the ratio M was less than 0.2 mol % (Experimental Example 17). Further, the melt temperature was sufficiently low, but the thermal conductivity decreased and the minimum melt viscosity decreased significantly in a case where the ratio M was greater than 16.3 mol % (Experimental Example 18). In this case, it was difficult to shape the resin composition due to the excessive flow of the resin composition upon the manufacturing of the resin substrate 50, attributed to the excessively-low minimum melt viscosity.

In contrast, in cases where the ratio M was 0.2 mol % to 16.3 mol % (Experimental Examples 1 to 16), the melt temperature and the minimum melt viscosity were both sufficiently low while the high thermal conductivity was maintained. These results show that, when the ratio M is made appropriate in a case where the resin composition includes the first curing agent and the second curing agent together, the increase in the thermal conductivity, involved in the heat-conducting property, and the improvement in the melt temperature and the minimum melt viscosity, which are involved in the formability, are both achieved.

In these cases, in particular, the thermal conductivity was further increased while the melt temperature and the minimum melt viscosity were both sufficiently low when the ratio M was 0.2 mol % to 5.0 mol % (Experimental Examples 1 to 4 and 7).

In addition, in a case where the second curing agent included the methoxy group as the alkoxy group (Experimental Example 7), the melt temperature and the minimum melt viscosity were both further decreased while the high thermal conductivity was maintained as compared with a case where the second curing agent included the propoxy group as the alkoxy group (Experimental Example 16), even though values thereof of the ratio M were about the same as each other.

As can be seen from the results illustrated in the Tables 1 and 2, the heat-conducting property and the formability were both achieved when the resin composition included the epoxy compound, the first triphenylbenzene compound expressed by the expression (1), and the second triphenylbenzene compound expressed by the expression (2), and the ratio M was in the appropriate range. Hence, a superior thermal characteristic was obtained.

Although the invention has been described by referring to one embodiment and the Examples, the invention is not limited to those described in one embodiment and the Examples, and may be modified in a wide variety of ways.

This application is based upon and claims the benefit of priority of the Japanese Patent Application No. 2015-091609 filed with the Japan Patent Office on Apr. 28, 2015 and the Japanese Patent Application No. 2016-086708 filed with the Japan Patent Office on Apr. 25, 2016, the entire contents of which are incorporated herein by reference.

It should be understood by those skilled in the art that various modifications, combinations, sub-combinations, and alterations may occur depending on design requirements and other factors insofar as they are within the scope of the appended claims or the equivalents thereof.

The invention claimed is:
1. A resin composition comprising:
an epoxy compound;
a first triphenylbenzene compound represented by the following expression (1); and
a second triphenylbenzene compound represented by the following expression (2),

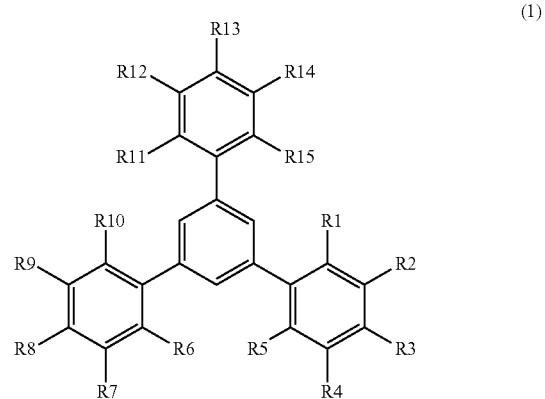

where R1 to R15 are each independently selected from the group consisting of a hydrogen group (—H) and a hydroxyl group (—OH) so long as two or more of R1 to R15 are hydroxyl groups,

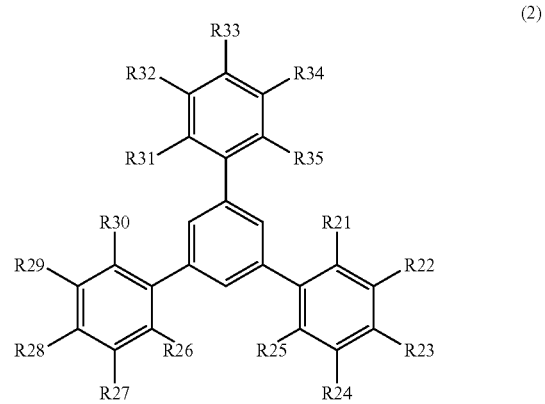

where R21 to R35 are each independently selected from the group consisting of a hydrogen group, a hydroxyl group, and an alkoxy group so long as at least one of R21 to R35 is a hydroxyl group, and at least one of R21 to R35 is an alkoxy group, wherein a ratio M (mol %) expressed by the following mathematical expression (A) is in a range of from 0.2 mol % to 16.3 mol %, $$M(\text{mol \%}) = (M1/M2) \times 100 \tag{A}$$

where:
M1 is the number of moles (mol) of the alkoxy group contained in the second triphenylbenzene compound, and
M2 is a sum of the number of moles (mol) of the hydroxyl group contained in the first triphenylbenzene compound, the number of moles (mol) of the hydroxyl group contained in the second triphenylbenzene compound, and the number of moles (mol) of the alkoxy group contained in the second triphenylbenzene compound.

2. The resin composition according to claim 1, wherein the ratio M is in a range of from 0.2 mol % to 5.0 mol %.

3. The resin composition according to claim 1, wherein
at least one of R1 to R5 is a hydroxyl group,
at least one of R6 to R10 is a hydroxyl group, and
at least one of R11 to R15 is a hydroxyl group.

4. The resin composition according to claim 1, wherein
one of R1 to R5 is a hydroxyl group,
one of R6 to R10 is a hydroxyl group, and
one of R11 to R15 is a hydroxyl group.

5. The resin composition according to claim 1, wherein the first triphenylbenzene compound includes a compound represented by the following expression (1-1):

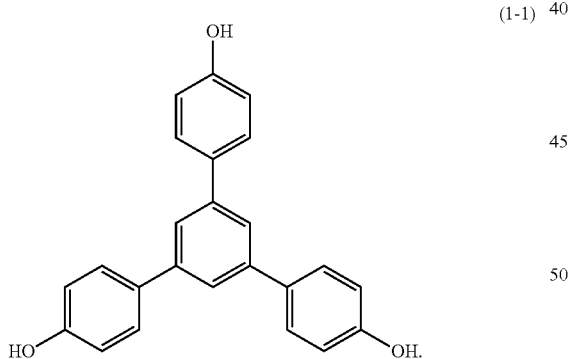
(1-1)

6. The resin composition according to claim 1, wherein the alkoxy group is any one of a methoxy group (—OCH$_3$), an ethoxy group (—OC$_2$H$_5$), and a propoxy group (—OC$_3$H$_7$).

7. The resin composition according to claim 1, wherein a sum of the number of hydroxyl groups and the number of alkoxy groups contained in the second triphenylbenzene compound (a single molecule) is three.

8. The resin composition according to claim 1, wherein the second triphenylbenzene compound includes at least one of compounds represented by the following respective expressions (2-1) to (2-6):

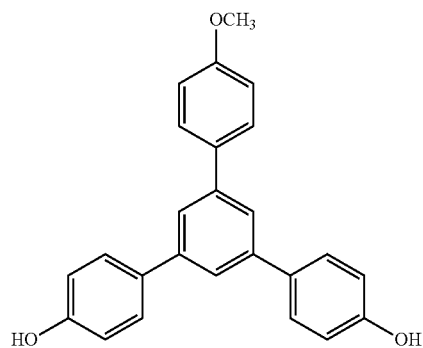
(2-1)

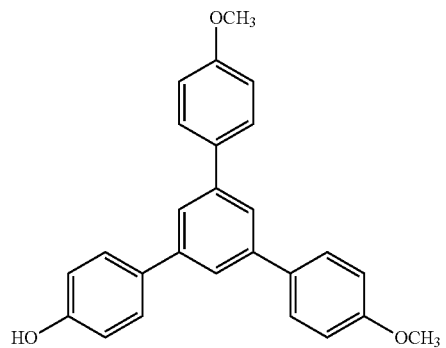
(2-2)

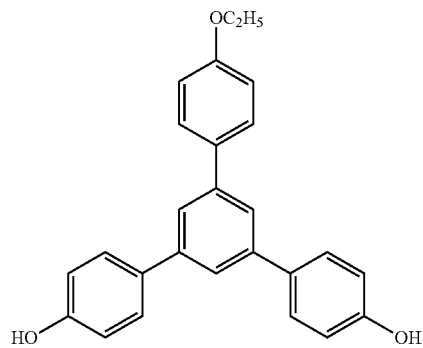
(2-3)

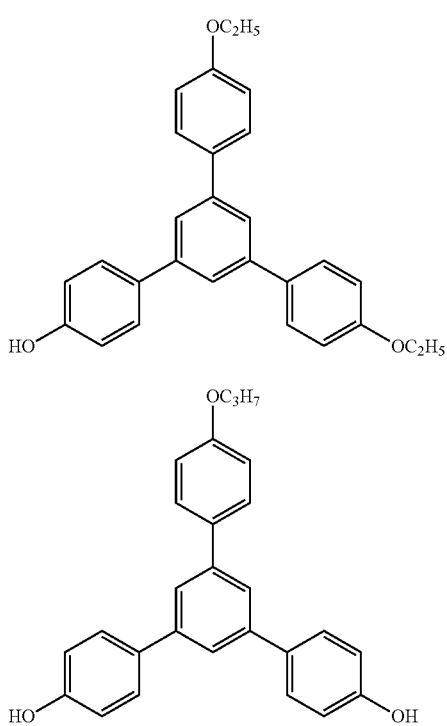

(2-4)

(2-5)

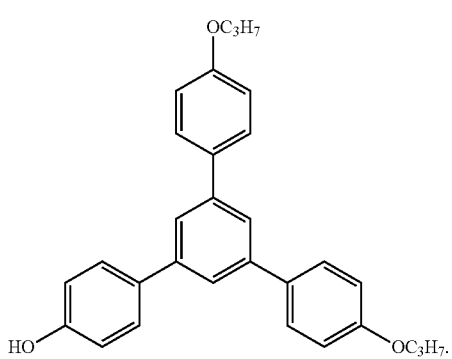

(2-6)

9. A resin cured product comprising a cured reactant of the resin composition according to claim 1.

10. A resin sheet comprising the resin composition according to claim 1.

11. A resin substrate comprising a cured reactant of the resin sheet according to claim 10.

12. The resin substrate according to claim 11, wherein the cured reactant comprises two or more cured reactants of the resin sheets, and the two or more cured reactants of the resin sheets are stacked.

\* \* \* \* \*